(12) United States Patent
Curry et al.

(10) Patent No.: US 8,622,064 B2
(45) Date of Patent: Jan. 7, 2014

(54) COMBINATION TOOTHPICK AND MINT DISPENSER

(76) Inventors: Scott Curry, San Marcos, CA (US); Rich Dicker, San Diego, CA (US)

( * ) Notice: Subject to any disclaimer, the term of this patent is extended or adjusted under 35 U.S.C. 154(b) by 0 days.

(21) Appl. No.: 12/824,203

(22) Filed: Jun. 27, 2010

(65) Prior Publication Data

US 2011/0315571 A1    Dec. 29, 2011

(51) Int. Cl.
*A61C 15/00*    (2006.01)

(52) U.S. Cl.
USPC ............................................. 132/329

(58) Field of Classification Search
USPC ................ 132/321, 322, 328, 329, 309, 311; 206/538, 469, 528, 535; 401/132–135; 222/189.01, 541.3, 541.4, 94, 105, 222/131, 420
See application file for complete search history.

(56) References Cited

U.S. PATENT DOCUMENTS

| | | | |
|---|---|---|---|
| 2,931,370 A | | 4/1960 | Jackson |
| 4,229,482 A | * | 10/1980 | Kreske, Jr. .................... 426/134 |
| 5,071,033 A | | 12/1991 | Siwek |
| 5,382,364 A | * | 1/1995 | Bowser et al. ................ 210/640 |
| 5,829,645 A | * | 11/1998 | Hennemann ............ 222/189.09 |
| 5,850,919 A | * | 12/1998 | Freed ............................. 206/534 |
| 5,915,392 A | | 6/1999 | Isaac |
| 6,220,479 B1 | | 4/2001 | Fishman |
| 6,554,522 B1 | | 4/2003 | Connelly |
| 7,004,350 B2 | | 2/2006 | Oroumieh |
| 7,066,349 B2 | | 6/2006 | Cohen |
| 7,204,391 B2 | | 4/2007 | Toker |
| 2003/0019062 A1 | * | 1/2003 | Florence ...................... 15/167.1 |
| 2004/0163663 A1 | | 8/2004 | Cooper |
| 2005/0098193 A1 | | 5/2005 | Tsaur |
| 2006/0070646 A1 | | 4/2006 | Denman |
| 2006/0225766 A1 | * | 10/2006 | Iderstine ....................... 132/322 |
| 2007/0034226 A1 | * | 2/2007 | Ferkel ............................ 132/329 |
| 2007/0095848 A1 | * | 5/2007 | Galland et al. ................ 220/784 |
| 2007/0286929 A1 | * | 12/2007 | Andersen ...................... 426/134 |
| 2009/0152295 A1 | * | 6/2009 | May et al. ...................... 222/129 |
| 2009/0205674 A1 | | 8/2009 | Saloff |

OTHER PUBLICATIONS

GE Water & Process Technologies, GE Nylon Hydrophobic Membrane, Jan. 2009, GE, FS1063EN.doc, p. 1.*

* cited by examiner

*Primary Examiner* — Nicholas Lucchesi
*Assistant Examiner* — Niyati D Shah
(74) *Attorney, Agent, or Firm* — Muskin & Farmer LLC

(57) ABSTRACT

A combination toothpick and mint dispenser. On a bottom end of the dispenser is a toothpick. On a top end (opposite the bottom end) is a chamber which is used to hold solid mints or liquid refreshment (such as mouthwash). In an embodiment, a shaft connecting the chamber to the toothpick can be hollow, thereby allowing liquid refreshment to pass from the chamber through a bottom of the shaft and out of the dispenser.

12 Claims, 7 Drawing Sheets

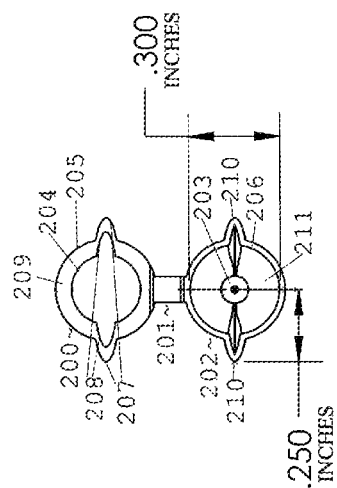

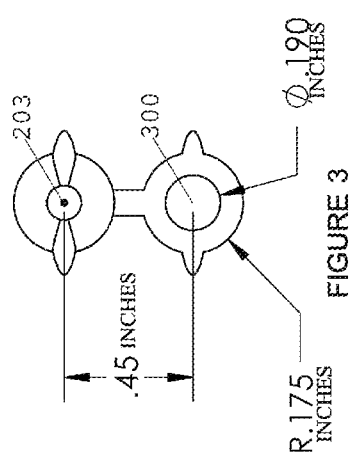

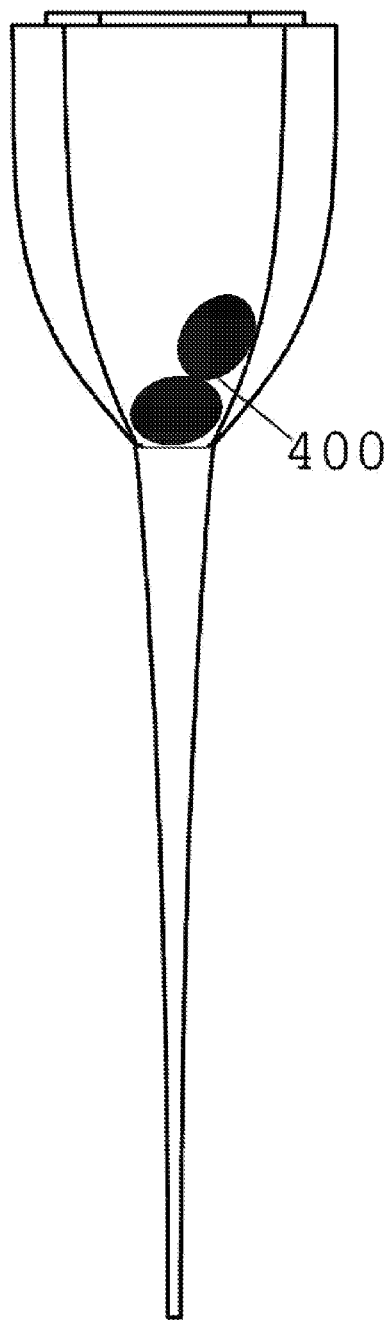
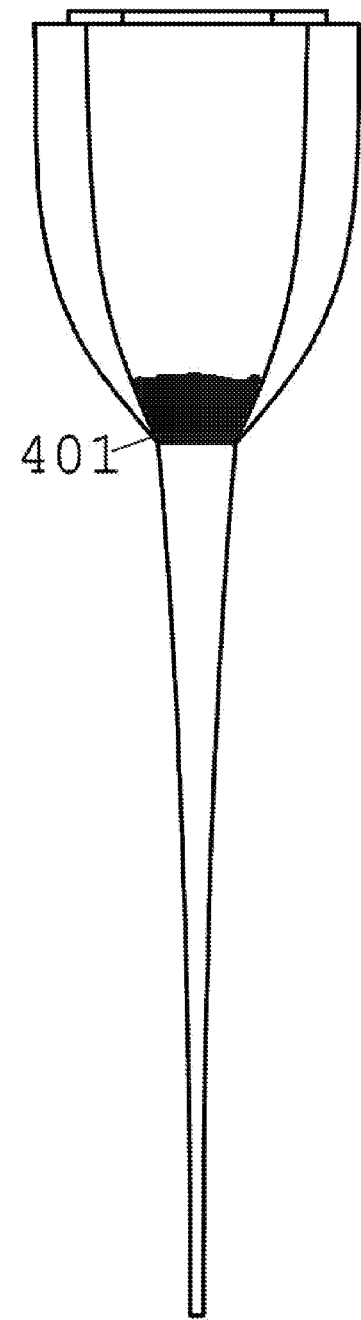
FIGURE 4A                    FIGURE 4B

COMBINATION TOOTHPICK AND MINT DISPENSER

BACKGROUND OF THE INVENTION

1. Field of the Invention

The present general inventive concept is directed to a method and apparatus, for storing and dispensing mints (both liquid and solid).

2. Description of the Related Art

Toothpicks and mints are products that are customarily dispensed separately at restaurants. What is needed is a way to combine these two products in a manner that is convenient for the restaurant owner (and other establishments) while being easy to use and desirable for the end-user.

SUMMARY OF THE INVENTION

It is an aspect of the present invention to provide an integrated toothpick and individual mint dispenser.

The above aspects can be obtained by (a) a chamber with a lid, the lid adapted to form an airtight seal around the chamber when in a closed position; (b) an edible refreshment located inside the chamber; (c) a shaft with a top end and a bottom end, the top end connected to the chamber; and (d) a toothpick connected to a bottom end of the shaft.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which:

FIG. 2 is a top view of a combination toothpick and mint dispenser and a lid, according to an embodiment;

FIG. 3 is a further top view of a combination toothpick and mint dispenser and a lid, according to an embodiment;

FIG. 4A is a side view of a closed combination toothpick and mint dispenser with solid mints, according to an embodiment;

FIG. 4B is a side view of a closed combination toothpick and mint dispenser with liquid mint, according to an embodiment;

DESCRIPTION OF THE PREFERRED EMBODIMENTS

Figure 1:
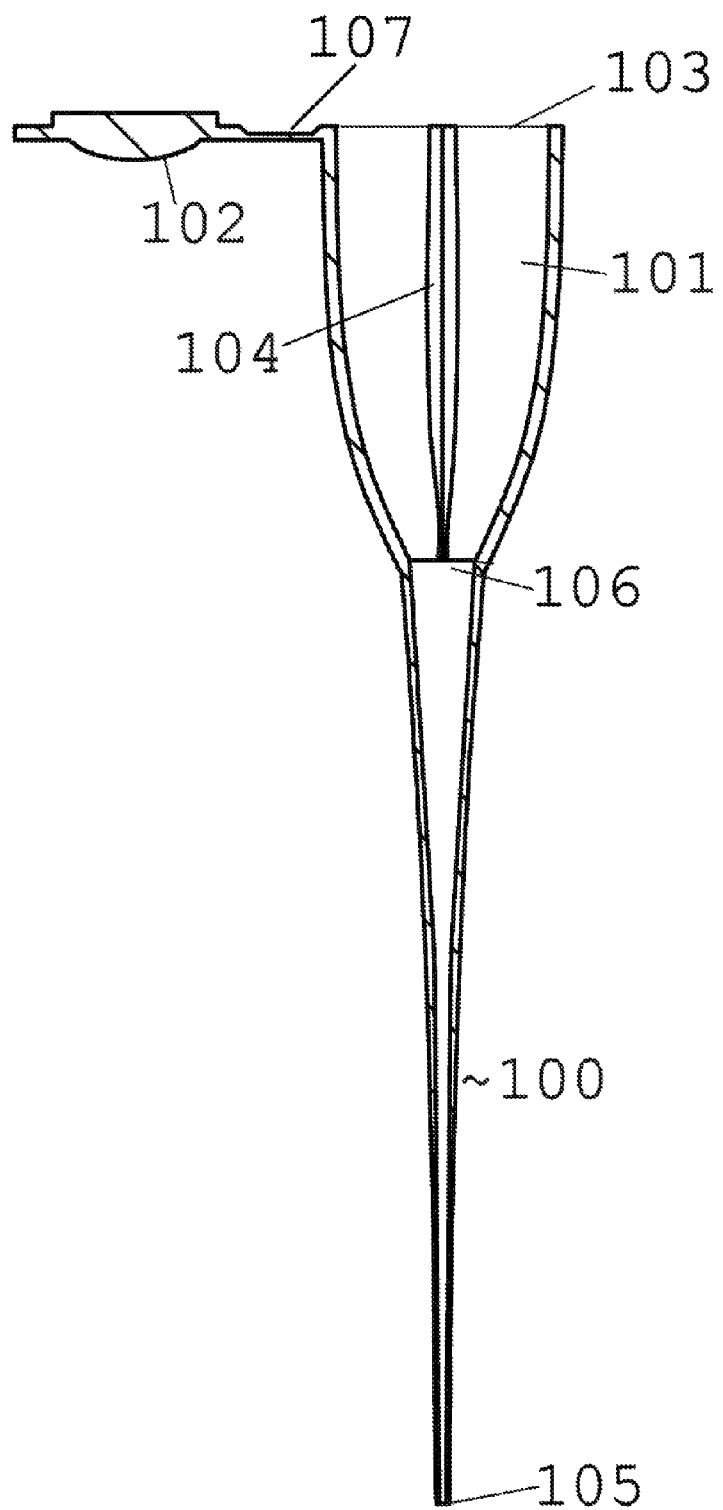
FIG. 1 is a front view of a combination toothpick and mint dispenser, according to an embodiment.

Reference will now be made in detail to the presently preferred embodiments of the invention, examples of which are illustrated in the accompanying drawings, wherein like reference numerals refer to like elements throughout.

The present inventive concept relates to a method and apparatus to conveniently combine a mint dispenser (either liquid or solid) with a toothpick so that a user can both use the toothpick as well as eat mints (or drink liquid mint or other liquid). The dispenser can be disposable. The inventive concept described herein can also be used as a pipette which can be used to dispense medicine.

FIG. 1 is a front view of a combination toothpick and mint dispenser, according to an embodiment.

A combination toothpick and mint dispenser 100 has a narrow toothpick tip 105 which can be used as a toothpick. The dispenser 100 can be made entirely of plastic. The dispenser 100 has a chamber 101 to store the mints (liquid or solid) and a lid 102 which can seal the chamber 101 thereby protecting the contents inside. An opening 103 on top of the chamber 101 allows the contents (mints) to be poured outside of the chamber (or sucked) into a user's mouth. When the lid 102 is secured onto the chamber 101 the contents of the chamber should be airtight. A fin 104 is used to allow the user to easily grip and open the lid 102 using the user's tongue, fingers, or teeth. A hinge 107 allows the lid 102 to open and close (when closed the lid 102 fits onto the opening 103). A shaft 106 runs from the chamber 101 to the toothpick tip 105. The shaft 106 can be solid for when solid mints are stored inside the chamber 211 and are removed by opening the lid 200. Alternatively, the shaft 106 can also be hollow, for when liquid is stored in the chamber 211 and can be sucked through the shaft 203 and out through a bottom of the shaft. In the latter embodiment, the toothpick tip 105 can be broken off by the user to expose the shaft 106 (in this case hollow) so the liquid can be sucked out.

FIG. 2 is a top view of a combination toothpick and mint dispenser and a lid, according to an embodiment.

A lid 200 is adapted to snap fit to seal the chamber 211 thereby seal the contents thereof. A neck 201 connects (attaches) the lid 200 to the dispenser 202. A shaft 203 is in the center of the chamber 211. An inner indent 204 and an outer indent 205 are molded on the lid 200 and are adapted to snap (friction) fit onto a chamber perimeter 206. A lid gap 209 is a gap between the inner indent 204 and the outer indent 205 and is adapted to receive the perimeter 206. Outer fins 207 are located on the outer indent 205 and inner fins 208 are located on the inner indent 204 which are adapted to snap onto perimeter fins 210 on the perimeter 206. The outer fins 207 provide a greater surface area and should typically make it easier for a user to open the lid 200 by grabbing onto the outer fins 207 with the user's fingers, tongue, teeth, etc. With the lid 200 open, the chamber 211 is exposed to the air thereby allowing the contents therein to be removed.

FIG. 3 is a further top view of a combination toothpick and mint dispenser and a lid, according to an embodiment.

In one embodiment, a distance between a center of the shaft 203 and a center of the lid 300 is 0.45 inches and a radius of the outer indent of the lid is 0.175 inches. It is noted that all measurements described herein merely reflect one embodiment, but the inventive concepts described herein can be constructed using other measurements as well. The measurements used herein are merely one example. All measurements herein are shown in inches.

FIG. 4A is a side view of a closed combination toothpick and mint dispenser with solid mints, according to an embodiment.

Mints 400 (also known as refreshments) are shown in a chamber and can be removed by opening a lid on top of the dispenser (the lid being described herein). The shaft in this embodiment would typically be solid, although in another embodiment the shaft can be hollow although the mints would typically be too large to suck through the shaft.

FIG. 4B is a side view of a closed combination toothpick and mint dispenser with liquid mint, according to an embodiment.

Liquid refreshment 401 (mouthwash, medicine, liquor, etc.) is located in the chamber. The liquid used herein can also be medicine (e.g., antibiotic, cough medicine, etc.) There are numerous possible embodiments for use with liquid refreshment. A lid (as described herein) can be used, which can be opened and the liquid can be sucked out directly from the chamber (without going through the shaft). Alternatively, no lid can be present (the chamber is molded closed) and the only way to access the liquid 401 would be for the user to suck it out of the shaft (this will be discussed below in more detail). Alternatively, a lid (as described herein) can be used in combination with a hollow shaft (as described herein), and the user can choose whether to open the lid and remove the liquid that way or to leave the lid shut and suck the liquid out of the shaft.

While the liquid refreshment 401 may possibly seep down the shaft (even when the bottom of the shaft is sealed), the viscosity of the liquid refreshment may prevent the liquid refreshment 401 from falling down into the shaft until a user intentionally breaks a seal on a bottom of the shaft and sucks the liquid refreshment 401 out through an opening on the bottom of the shaft (the opening passing through the length of the shaft making the shaft hollow like a straw). Alternatively, a chamber membrane can be used to prevent the liquid refreshment 401 from falling down into the shaft (See FIGS. 7A, 7B and their respective descriptions).

The term "refreshment" can refer to either solid mint(s) or any suitable liquid. The bottom of the shaft in both FIGS. 4A and 4B can typically have a pointed end (a toothpick). The toothpick can be made of plastic or alternatively a wooden toothpick can be used which can be inserted into an opening at a bottom of the shaft.

Figure 5:
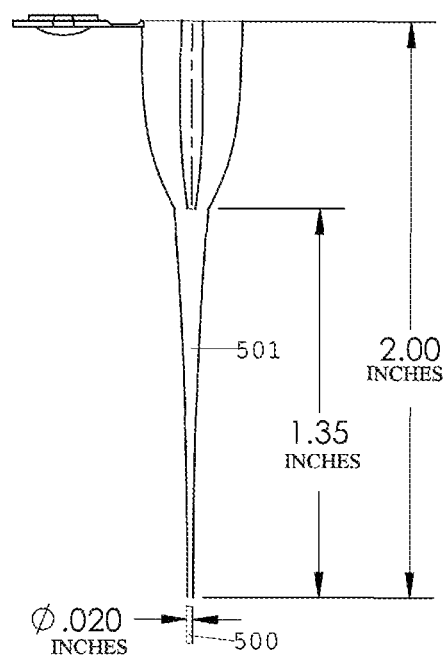
FIG. 5 is a front view of a combination toothpick and mint dispenser with a bottom opening, according to an embodiment.

FIG. 5 is a front view of a combination toothpick and mint dispenser with a bottom opening, according to an embodiment.

A hollow shaft 501 is used so that a user can suck out contents of the chamber (typically liquid) through the shaft 501 and out a bottom opening in the shaft 501 (the top being the lid). Toothpick tip 500 can be intentionally broken off a bottom of the shaft 501 by the user, thereby exposing the hollow shaft 501 and allowing the user to suck out the liquid from the chamber through the bottom of the shaft. While an opened lid is shown in this Figure, in the embodiment with a hollow shaft so that the liquid can be sucked out the shaft, an openable lid can be optional (alternatively a top of the chamber can be permanently sealed or molded shut).

Figure 6:
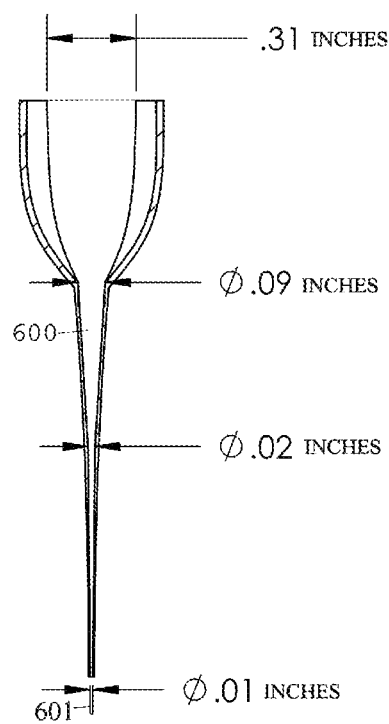
FIG. 6 is a side view of a combination toothpick and mint dispenser with a bottom opening, according to an embodiment.

FIG. 6 is a side view of a combination toothpick and mint dispenser with a bottom opening, according to an embodiment.

In a further embodiment, contents of in the chamber can be sucked through a hollow shaft 600 and out an opening in a bottom of the hollow shaft 600. A removable shaft plug 601 is physically narrower than the dimensions of a bottom of the hollow shaft 600 so that the shaft plug 601 can be removed from the hollow shaft 600 simply by a user removing it with his or her fingers. The shaft plug 601 can also serve as a toothpick (either while attached to the shaft 600 or after being removed from the shaft 600). Once the shaft plug 601 is removed, liquid from the chamber can then be sucked out of the opening in the bottom of the hollow shaft 600. In this embodiment, the chamber can be molded closed (sealed) without an openable lid (since the liquid should be sucked out the shaft 600), although in an alternate embodiment a lid (as described herein) can be used giving the user the option of whether to remove the liquid by opening the lid or sucking it out of the shaft 600.

Figure 7A:
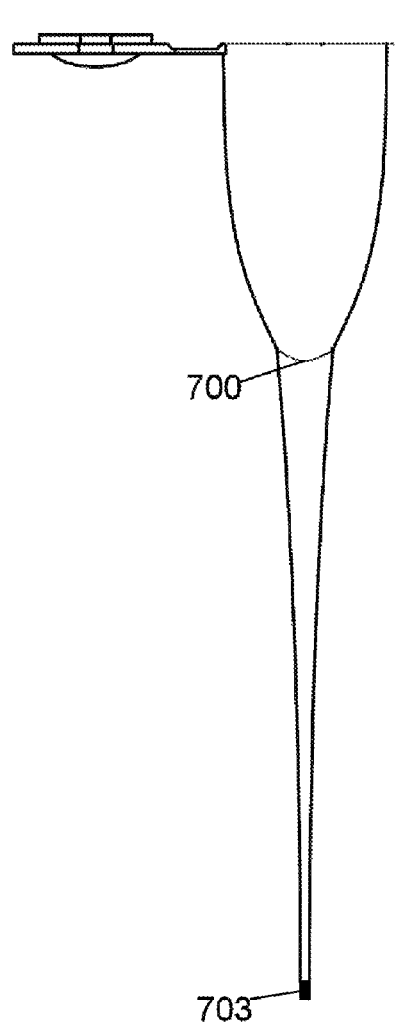
FIG. 7A is a side view of a combination toothpick and dispenser with a chamber membrane and edible tip, according to an embodiment.

FIG. 7A is a side view of a combination toothpick and dispenser with a chamber membrane and edible tip, according to an embodiment.

A chamber membrane 700 can be used to separate the liquid (not pictured in FIG. 7A) in the chamber from the shaft so that the liquid is prevented from seeping into and down the shaft. The chamber membrane 700 can be made from an easily breakable material, such as a thin layer of plastic or rubber. A user can eat (for break) off an edible tip 703 which can be made of any edible material such as chocolate, wax, etc., thereby exposing the hollow shaft. The user can then suck air out of the shaft which will then cause the chamber membrane 700 to break, thereby causing the liquid (not pictured in FIG. 7A) to flow into the shaft. The user can continue to suck the shaft which causes the liquid to flow through the shaft and out of an end of the shaft and thus into the user's mouth.

Note that the lid is open in FIG. 7A, this is because without a flow of air into the chamber, it may be difficult or impossible to suck the liquid out of the chamber and through the shaft. Thus, the user should typically position the lid (which can be in both an open and a closed position) into the open position when the user wishes to suck the liquid out of the shaft.

Figure 7B:
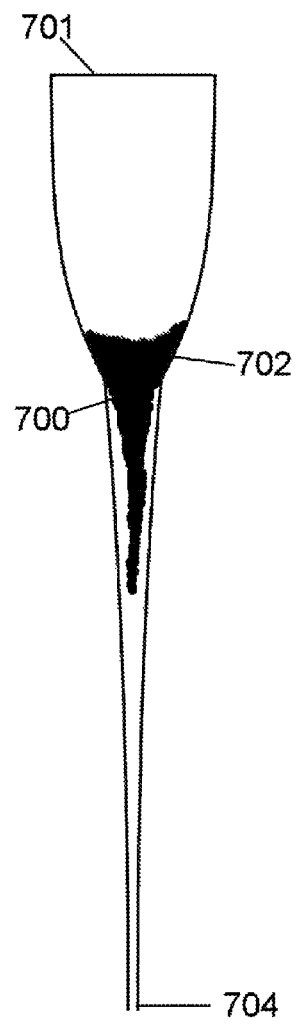
FIG. 7B is a side view of a combination toothpick and dispenser with a hydrophobic membrane, broken chamber membrane, and liquid, according to an embodiment.

FIG. 7B is a side view of a combination toothpick and dispenser with a hydrophobic membrane, broken chamber membrane, and liquid, according to an embodiment.

Instead of the lid, a hydrophobic membrane 701 (for example polytetrafluoroethylene or GE Nylon) can be used to cover the top of the chamber. The hydrophobic membrane can be a permeable membrane of that type that can let air into the chamber while preventing the liquid 702 in the chamber from passing through the hydrophobic membrane (even when the liquid is positioned directly adjacent to the hydrophobic membrane). Using the hydrophobic membrane obviates the need for the user to physically open a lid on the chamber (thus in this embodiment, no lid would be needed or used on the chamber), as air can pass from outside the chamber through the hydrophobic membrane into the chamber thereby preventing a vacuum condition from existing inside the chamber which would prevent the liquid from exiting through the shaft.

FIG. 7B shows the combination toothpick and dispenser with the edible tip 703 broken off and a broken chamber membrane 700 (not visible in FIG. 7B because it is covered by liquid 702). The chamber membrane 700 may break automatically upon breaking off of the edible tip 703 or may require more force such as a sucking force by the user from the end 704 of the tip in order to break the chamber membrane. The liquid 702 can then flow through the shaft (either freely or by force of sucking from the end 704) and out the end 704 and into the user's mouth.

It is noted that all features described herein can be combined with one-another to create embodiments using any combination of the features described herein. It is further noted that the devices described herein can be entirely made of plastic or other suitable material and such devices can be made using known manufacturing processes such as injection molding.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. An apparatus, comprising:
    a chamber with a lid, wherein the lid comprises an inner indent and an outer indent with a gap between the inner indent and the outer indent, and the chamber comprises a perimeter, wherein in a closed position the perimeter forms a friction fit inside the gap between the inner indent and the outer indent forming an airtight seal around the chamber;
    a pair of opposing fins on the lid and a second pair of opposing fins on the perimeter of the chamber, each of said fin in the pair of opposing fins protruding externally from the chamber and the lid, each of said fin in the pair of opposing fins of the lid defined by the inner indent and the outer indent and having a cooperating portion on the pair of opposing fins of the perimeter on the chamber, the opposing fins on the lid configured to snap onto the cooperating portion of the opposing fins on the perimeter thereby sealing the chamber;
    a hinge attached to the lid configured to enable the lid to swing open and closed, where in the closed position the pair of opposing fins of the lid is aligned with the cooperating portion of the pair of opposing fins of the perimeter of the chamber;
    an edible refreshment located inside the chamber;
    a shaft with a top end and a bottom end, the top end connected to the chamber; and
    a toothpick connected to a bottom end of the shaft.

2. The apparatus as recited in claim 1, wherein the shaft is solid and the refreshment is at least one solid mint.

3. The apparatus as recited in claim 1, wherein the shaft is hollow and the refreshment is liquid.

4. The apparatus as recited in claim 3, wherein the toothpick is breakable at the bottom end of the shaft, and when the toothpick is broken off an opening inside the shaft is exposed, thereby allowing the liquid to pass from the chamber through the shaft and out of the opening.

5. The apparatus as recited in claim 3, wherein the toothpick is removably inserted into an opening at the bottom end of the shaft, and when the toothpick is removed the opening inside the shaft is exposed, thereby allowing the liquid to pass from the chamber through the shaft and out of the opening.

6. An apparatus comprising:
    a chamber comprising a liquid;
    a hydrophobic membrane covering a top of the chamber, the hydrophobic membrane configured to allow air to pass through the membrane into the chamber while not allowing the liquid to pass through the membrane;
    a chamber membrane on a bottom of the chamber; and
    a hollow shaft comprising a top end connected to said bottom of the chamber and a bottom end, the hollow shaft initially containing no liquid;
    wherein exerting pressure on the chamber membrane causes the chamber membrane to break, thereby causing the liquid to flow through the hollow shaft;
    a toothpick tip connected to said bottom end of the hollow shaft.

7. The apparatus as recited in claim 6, further comprising an edible tip attached to the bottom end.

8. The apparatus as recited in claim 6, wherein the liquid is medicine.

9. The apparatus as recited in claim 6, wherein the liquid is mouthwash.

10. The apparatus as recited in claim 6, wherein the pressure exerted onto the chamber membrane is caused by a user sucking out of the bottom end of the shaft.

11. The apparatus as recited in claim 6, wherein the hydrophobic membrane is made of polytetrafluoroethylene.

12. The apparatus as recited in claim 6, wherein the hydrophobic membrane is made of GE Nylon.

* * * * *